United States Patent
Cheng et al.

(10) Patent No.: US 12,221,410 B2
(45) Date of Patent: Feb. 11, 2025

(54) METHOD FOR PREPARING PINACOLONE

(71) Applicant: HEZE BRANCH, QILU UNIVERSITY OF TECHNOLOGY(SHANDONG ACADEMY OF SCIENCES), Heze (CN)

(72) Inventors: Wei Cheng, Heze (CN); Fengke Yang, Heze (CN); Zhiyuan Zhao, Heze (CN); Shoufeng Li, Heze (CN); He Ma, Heze (CN); Xinfang Ge, Heze (CN); Yinuo Wei, Heze (CN); Yanchao Yin, Heze (CN); Li Liu, Heze (CN)

(73) Assignee: HEZE BRANCH, QILU UNIVERSITY OF TECHNOLOGY(SHANDONG ACADEMY OF SCIENCES), Heze (CN)

( * ) Notice: Subject to any disclaimer, the term of this patent is extended or adjusted under 35 U.S.C. 154(b) by 0 days.

(21) Appl. No.: 18/667,200

(22) Filed: May 17, 2024

(65) Prior Publication Data
US 2024/0360064 A1 Oct. 31, 2024

Related U.S. Application Data

(63) Continuation of application No. PCT/CN2022/094219, filed on May 20, 2022.

(30) Foreign Application Priority Data

Nov. 22, 2021 (CN) .......................... 202111388133.7

(51) Int. Cl.
- C07C 45/45 (2006.01)
- B01J 23/10 (2006.01)
- C07C 17/08 (2006.01)

(52) U.S. Cl.
CPC ............... *C07C 45/45* (2013.01); *B01J 23/10* (2013.01); *C07C 17/08* (2013.01)

(58) Field of Classification Search
CPC ...................................................... C07C 45/45
See application file for complete search history.

(56) References Cited

U.S. PATENT DOCUMENTS

| | | | |
|---|---|---|---|
| 4,057,583 | A | 11/1977 | Merz et al. |
| 4,224,252 | A | 9/1980 | Kyo et al. |

FOREIGN PATENT DOCUMENTS

| | | |
|---|---|---|
| CN | 101148401 A | 3/2008 |
| CN | 102886278 A | 1/2013 |

(Continued)

OTHER PUBLICATIONS

Patent No. CN107628935A; machine translation, Jan. 1, 2018; pp. 1-16 (Year: 2018).*

(Continued)

*Primary Examiner* — Medhanit W Bahta

(57) ABSTRACT

A method for preparing pinacolone is provided. Raw materials including 2-methyl-2-butene, hydrochloric acid and formaldehyde are reacted in the presence of a catalyst to produce pinacolone. The catalyst is a single lanthanide Lewis acid, a compounded lanthanide Lewis acid or a lanthanide metal oxide soluble in hydrochloric acid. The lanthanide Lewis acid is lanthanum chloride, cerium chloride, praseodymium chloride, neodymium chloride, erbium chloride, holmium chloride, dysprosium chloride or thulium chloride. The method is performed through a continuous two-step reaction. In the first reaction, 2-methyl-2-butene and hydrochloric acid are reacted to form an intermediate, which undergoes a second reaction with formaldehyde in the presence of the catalyst to produce pinacolone.

16 Claims, 5 Drawing Sheets

(56) References Cited

FOREIGN PATENT DOCUMENTS

| CN | 103240094 A | | 8/2013 |
|---|---|---|---|
| CN | 104387250 A | | 3/2015 |
| CN | 105348055 A | | 2/2016 |
| CN | 105503550 A | | 4/2016 |
| CN | 106365964 A | | 2/2017 |
| CN | 106397150 A | | 2/2017 |
| CN | 106478390 A | | 3/2017 |
| CN | 107628935 A | * | 1/2018 |
| CN | 109809972 A | | 5/2019 |
| CN | 113956142 A | | 1/2022 |
| EP | 0085996 A2 | | 8/1983 |

OTHER PUBLICATIONS

PubChem "3-Methyl-1-butene", Mar. 27, 2005; pp. 1-2 (Year: 2005).*

PubChem "2-Methyl-2-butene", Mar. 26, 2005; pp. 1-2 (Year: 2005).*

\* cited by examiner

METHOD FOR PREPARING PINACOLONE

CROSS-REFERENCE TO RELATED APPLICATIONS

This application is a continuation of International Patent Application No. PCT/CN2022/094219, filed on May 20, 2022, which claims the benefit of priority from Chinese Patent Application No. 202111388133.7, filed on Nov. 22, 2021. The content of the aforementioned application, including any intervening amendments thereto, is incorporated herein by reference in its entirety.

TECHNICAL FIELD

This application relates to chemicals, and more particularly to a method for preparing pinacolone.

BACKGROUND

Pinacolone is an important intermediate in the production of agrochemicals, medicines, dyes and biological inhibitors, especially playing a crucial role in the preparation of triazole pesticides, anti-HIV drug Atazanavir, antifungal drug Terbinafine and antiepileptic drug Stiripentol. The existing preparation employs 2-methyl-2-butene as a raw material, which undergoes an addition reaction with industrial hydrochloric acid to prepare 2-chloro-2-methylbutane. After separation, the 2-chloro-2-methylbutane sequentially undergoes ring formation ring opening and rearrangement with a formaldehyde aqueous solution, and the resulting product is subjected to multiple distillation to obtain the pinacolone product. However, this method has a time-consuming production route and a low reaction yield, and moreover, the accompanied tar waste and hazardous waste acid will pose serious environmental pollution, resulting in high production cost. Further, the product purity is only about 95% (GC), and cannot meet the needs of pharmaceutical products. In the current industrial production, the yield of pinacolone is only about 77%, accompanied by 19% or more of the tar, which not only reflects the poor reaction selectivity, but also causes environmental and process control problems (referring to embodiment 2 of this application for specific parameters). The above-discussed defects seriously restrict the production expansion and industry development.

How to prepare pinacolone in an environmentally-friendly manner has attracted extensive attention. Chinese Patent Publication No. 109809972A published a green and continuous method for preparing pinacolone, which still cannot avoid the production of tar impurities. The brown tar impurities will be accumulated in the acidic water phase, which will seriously affect the production of pinacolone after being recycled, resulting in poor product quality. The tar impurities may be accumulated to form the hazardous distillation residue, and due to the accumulation of impurities, the waste acid is not suitable to be recycled. Therefore, this method still cannot address the of discharge of waste acid and tar impurities, and thus is not suitable for popularization.

Chinese Patent Publication No. 103240094A published a preparation method and composite catalyst for pinacolone, which uses 2-chloro-2-methylbutane as a raw material and a Zn/Co/Sb composite catalyst to prepare pinacolone. This method is a condensation reaction after separating an intermediate 2-chloro-2-methylbutane, and a separation step of the intermediate is inevitable. A reaction time of this method is 4-5 h, which is not significantly shortened, and a yield of product is not significantly improved. In addition, the method does not solve environmental problems that a large number of tar impurities and waste acid are produced in this production process, and environmental benefits of this method are not obvious.

Chinese Patent Publication No. 105503550A published a green method for preparing pinacolone, in which 2-methyl-2-butene is reacted with hydrochloric acid to obtain tert-amyl chloride, and the tert-amyl chloride is collected and reacted with triformol in a solvent, such as methanol and pinacolone, to obtain pinacolone. This process avoids the use of hydrochloride acid, thereby reducing the production of waste acid. However, it has been demonstrated that the condensation, ring formation and rearrangement reactions of tert-amyl chloride and triformol prefer an acid solvent, and the reaction yield is extremely low in methanol or pinacolone. At the same time, the use of methanol also increases the discharge of organic waste solvent. The tar impurities generated after distillation will form the organic and hazardous distillation residue. Besides, the generation and discharge of waste acid still cannot be avoided, which brings higher environmental protection costs, and fails to essentially enable the green production.

SUMMARY

In view of the above problems, it is necessary to improve and optimize the existing pinacolone production methods, so as to improve the reaction selectivity and yield of pinacolone, reduce the production of tar impurities and waste acid, and improve the product quality, thereby achieving the green, cost-effective and efficient production of pinacolone.

On the basis of extensive experimental studies, it has been accidentally found that introducing a lanthanide Lewis acid catalyst in the traditional 2-methyl-2-butene reaction system can solve the problem of tar impurities to some extent. Compared with the traditional process without catalysts or with other types of catalysts, it can significantly reduce the tar content.

Single lanthanum chloride is firstly employed as the catalyst, and the tar content is reduced from 19.75% (without the lanthanum chloride) to 8.23%, exhibiting a good tar reduction effect. This may be because the catalyst greatly accelerates the reaction, improves the reaction selectivity, and greatly reduce the generation of tar. In addition to the reduction of the tar impurities, the pinacolone yield and purity are also increased, which are unexpected effects brought by the lanthanum chloride catalyst. On this basis, various catalysts and their combinations are selected for test, and the results demonstrate that the following catalysts or combinations can significantly reduce the tar content, and improve the yield and purity of pinacolone product compared to the existing industrial production.

In an embodiment, the catalyst is a single lanthanide Lewis acid or a compounded lanthanide Lewis acid; and the lanthanide Lewis acid is a bromo-lanthanide metal salt or a chloro-lanthanide metal salt. Considering that the present disclosure selects hydrochloric acid as solvent for the reaction system, the chloro-lanthanide metal salt is preferred. In an embodiment, the lanthanide Lewis acid is lanthanum chloride, cerium chloride, praseodymium chloride, neodymium chloride, erbium chloride, holmium chloride, dysprosium chloride or thulium chloride.

In addition, a lanthanide oxide can be dissolved in hydrochloric acid to form a lanthanide chloride; and if the lanthanide oxide is more easily obtained in an actual industry, it can also be the catalyst.

In an embodiment, the single lanthanide Lewis acid is selected from the group consisting of lanthanum chloride, cerium chloride, praseodymium chloride and neodymium chloride.

In an embodiment, the compounded lanthanide Lewis acid is a combination of a first component and a second component; wherein the first component is selected from the group consisting of lanthanum chloride, cerium chloride, praseodymium chloride and neodymium chloride; the second component is selected from the group consisting of lanthanum chloride, cerium chloride, praseodymium chloride, neodymium chloride, erbium chloride, holmium chloride, dysprosium chloride, thulium chloride, and a combination thereof; and the second component is free of a compound selected as the first component, that is, when the first component is lanthanum chloride, the second component is selected from the group consisting of cerium chloride, praseodymium chloride, neodymium chloride, erbium chloride, holmium chloride, dysprosium chloride, thulium chloride, and a combination thereof, when the first component is cerium chloride, the second component is selected from the group consisting of lanthanum chloride, praseodymium chloride, neodymium chloride, erbium chloride, holmium chloride, dysprosium chloride, thulium chloride, and a combination thereof, when the first component is praseodymium chloride, the second component is selected from the group consisting of lanthanum chloride, cerium chloride, neodymium chloride, erbium chloride, holmium chloride, dysprosium chloride, thulium chloride, and a combination thereof, and when the first component is neodymium chloride, the second component is selected from the group consisting of lanthanum chloride, cerium chloride, praseodymium chloride, erbium chloride, holmium chloride, dysprosium chloride, thulium chloride, and a combination thereof.

In an embodiment, a molar ratio of the first component to the second component in the compounded lanthanide Lewis acid is needed to be adjusted based on a large number of experiments, which will affect the final reaction effects.

In an embodiment, the molar ratio of the first component to the second component in the compounded lanthanide Lewis acid is 1:10-10:1, which has better reaction results; when the molar ratio is expanded to 1:50-50:1, the reaction results are slightly worse in some intervals, but are in an acceptable range of industrial applications; in an embodiment, the molar ratio is 1:5-10:1, 1:3-10:1, 3:1-10:1 or 5:1-10:1; in an embodiment, the molar ratio is 3:1; and reaction results of various compounded catalysts in different molar ratios are provided in embodiments of the present disclosure.

In a case that the second component is a combination of two compounds respectively selected from the group consisting of lanthanum chloride, cerium chloride, praseodymium chloride, neodymium chloride, erbium chloride, holmium chloride, dysprosium chloride, thulium chloride, a molar ratio of the first component to one of the two compounds to the other of the two compounds is 1-5:1-3:1-3, preferably 1-3:1:1, and more preferably 3:1:1.

In an embodiment, a molar ratio of the catalyst to 2-methyl-2-butene is needed to control; a molar ratio of the catalyst to the 2-methyl-2-butene is 5-50:1000, preferably 10-50:1000, 20-50:1000, 30-50:1000, 40-50:1000, 20:1000 and 50:1000; reaction results of various molar ratios of various catalysts to the 2-methyl-2-butene are provided in the embodiments of the present disclosure.

The embodiments of the present disclosure provide various catalyst combinations and their molar ratios. It can be clearly seen from reaction result data that the content of the tar impurities is reduced and the yield and purity of the pinacolone are greatly improved compared with the prior art. For example, tar production is controlled below 12%, preferably below 10%, 9%, 8%, 7%, 6%, 5% and 4%, at the same time, the yield of the pinacolone can be controlled above 80%, preferably above 85% and 90%. All of pinacolone products obtained from the method of the present disclosure can reach more than 98.50%, which meet the purity requirement of the pinacolone products in pharmaceuticals.

The present disclosure provides a method for preparing pinacolone, comprising:

subjecting the 2-methyl-2-butene and the hydrochloric acid to a first reaction to obtain an intermediate; and adding formaldehyde and the catalyst to the intermediate followed by a second reaction to produce pinacolone; wherein the first reaction and the second reaction are performed in a continuous manner, realizing a one-pot operation and greatly improving industrial efficiency; on the basis of using of the catalyst, the content of the tar impurities in this method is greatly reduced; and because of high reaction conversion and the high purity of the pinacolone, an ideal product can be obtained through single distillation.

In order to optimize various reaction indexes, based on characteristics of reaction materials, such as a low boiling point of the 2-methyl-2-butene, the present disclosure optimizes various main reaction parameters.

In an embodiment, the first reaction is performed at 0-10° C. for 60-90 min.

In an embodiment, the second reaction is performed at 60-90° C. for 1-6 h, preferably at 80-90° C. for 4-6 h, and especially at 83° C. for 4 h.

In an embodiment, in the second reaction, an addition of the formaldehyde lasts for 0.5-3 h, preferably 2-3 h; and the formaldehyde is added slowly.

Based on good effects obtained by above reactions, the present disclosure optimizes the reaction materials to meet requirements of green production in practical industrial applications; in an embodiment, a formaldehyde aqueous solution is replaced by a paraformaldehyde hydrochloric acid solution; and a weight ratio of paraformaldehyde to hydrochloric acid is preferably 1:5-1:20, especially 1:5 or 1:10.

The embodiments of the present disclosure show reaction results obtained under various preferred proportions of the paraformaldehyde hydrochloric acid solution.

Based on the above optimized process conditions, the generated hydrochloric acid solution of the present disclosure will no longer contain tar impurities which are difficult to remove, and can be conveniently recycled. For example, the hydrochloric acid solution can be recycled directly into the reaction system, thereby reducing the discharge of waste acid and waste water.

In an embodiment, a reaction solution obtained from the second reaction is cooled to room temperature, and subjected to standing and layering, wherein a top layer is collected as the pinacolone product, and a bottom layer is a hydrochloric acid layer, which can be recycled for at most 60 times, preferably 2-40 times. When the hydrochloric acid layer is recycled more than 60 times, it can be treated as waste acid because its purity cannot meet the reaction need. In an embodiment, the hydrochloric acid layer is extracted with an organic solvent, such as dichloromethane and dichloroethane, supplemented with hydrogen chloride, and then recycled.

In summary, the pinacolone preparation method provided herein can greatly reduce the tar production in the reaction process, greatly improve the yield and purity of the pinacolone, significantly reduce the production cost, and improve the product quality. Besides, the method has simplified reaction operation and reasonable process. As a whole, the method realizes the clean and green production of the pinacolone, and has considerable economic benefits.

DETAILED DESCRIPTION OF EMBODIMENTS

The technical solutions of embodiments of this application will be clearly and fully illustrated with reference to the accompanying drawings. It is obvious that described herein are merely some embodiments of this application rather than all embodiments. Based on the embodiments of this application, other embodiments obtained by those of ordinary skill in the art without making creative effort shall fall within the scope of the present disclosure.

Sources of reagents of the embodiments are described as follows:
2-methyl-2-butene: Zibo Liantan Chemical Co., Ltd;
paraformaldehyde: Zibo Qixing Chemical Technology Co., Ltd;
catalyst: Shandong Desheng New Material Co., Ltd; and
hydrochloric acid is a by-product from other production lines, or is purchased.

The tar production in the following embodiments is measured as follows: the resulting reaction liquid is filtered and centrifuged, and the tar impurities are collected and weighed.

Example 1

Figure 1:
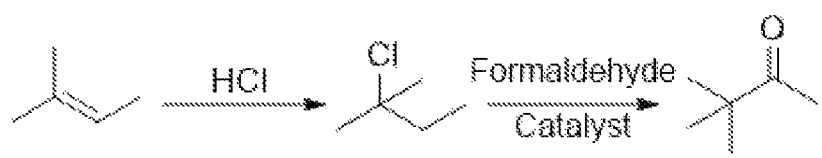
FIG. 1 is a reaction schematic diagram of a method for preparing pinacolone according to an embodiment of present disclosure.

The pinacolone preparation method of the present disclosure will be described in detail with reference to FIG. 1.

Figure 2:
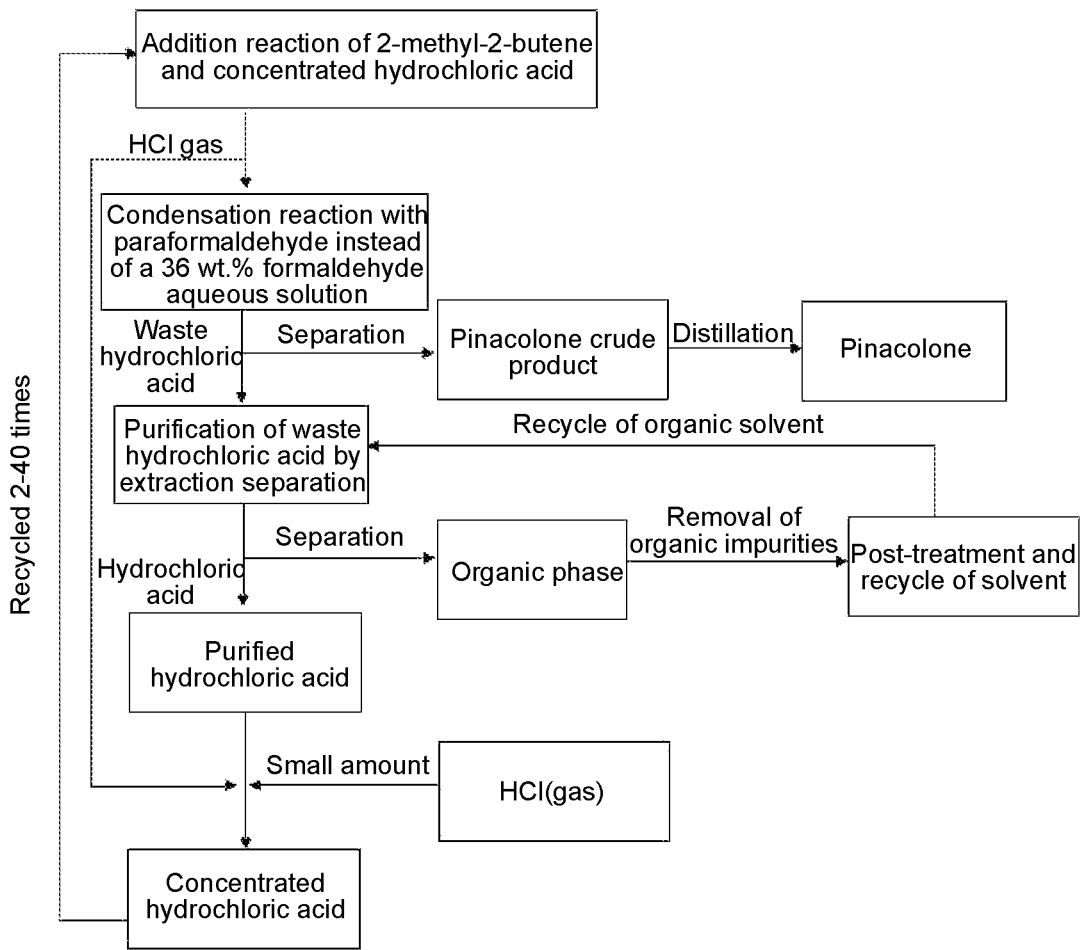
FIG. 2 is a flow chart of the method for preparing pinacolone according to an embodiment of present disclosure.

500 kg of a 30 wt. % industrial hydrochloric acid was added into a reaction vessel, and was cooled to 0-10° C. 160 kg of 2-methyl-2-butene, which was pre-cooled to −5° C., was slowly dropwise added into the reaction vessel under stirring. The reaction mixture was reacted at 0-10° C. for 60-90 min, and then heated to 50° C. The reaction mixture was added with a catalyst, dropwise added with 140 kg of a paraformaldehyde hydrochloric acid solution, heated to 60-90° C., reacted for 1-6 h, and cooled to room temperature. After that, the reaction mixture was subjected to standing and layering, where an upper organic phase was subjected to single distillation to obtain a pinacolone product, and a bottom hydrochloric acid layer was extracted with dichloromethane or dichloroethane, supplemented with hydrogen chloride, and then recycled (in this example, the bottom hydrochloric acid layer was recycled for 40 times). Specific reaction principle and reaction process were detailedly shown in FIGS. 1-2.

Example 2

According to the preparation method in Example 1, pinacolone was prepared respectively in the absence of a catalyst, and in the presence of a single lanthanide Lewis acid, compounded lanthanide Lewis acid, and other Lewis acid catalysts, where the catalyst (the total number of moles of ingredients for the compounded lanthanide Lewis acid) was 2% by mole of the 2-methyl-2-butene; the second reaction was performed at 83° C. for 4 h; and a weight ratio of paraformaldehyde to hydrochloric acid in the paraformaldehyde hydrochloric acid solution was 1:5. Experimental results were shown in Table 1.

TABLE 1

| | | | | Tar | | |
| | | Time | Temperature | production | Purity | Yield |
| Example | Catalyst | (h) | (° C.) | (%) | (%) | (%) |
| --- | --- | --- | --- | --- | --- | --- |
| 2.1 | — | 4 | 83 | 19.75 | 94.56 | 77.65 |
| 2.2 | Lanthanum chloride | 4 | 83 | 8.23 | 98.76 | 89.38 |
| 2.3 | Cerium chloride | 4 | 83 | 9.65 | 98.64 | 88.54 |
| 2.4 | Praseodymium chloride | 4 | 83 | 9.58 | 98.51 | 86.62 |
| 2.5 | Neodymium chloride | 4 | 83 | 8.64 | 98.58 | 87.54 |
| 2.6 | Erbium chloride | 4 | 83 | 9.14 | 98.50 | 87.05 |
| 2.7 | Holmium chloride | 4 | 83 | 9.51 | 98.38 | 85.52 |
| 2.8 | Dysprosium chloride | 4 | 83 | 8.82 | 98.52 | 84.66 |
| 2.9 | Thulium chloride | 4 | 83 | 9.27 | 97.81 | 84.97 |
| 2.10 | Lanthanum bromide | 4 | 83 | 11.53 | 97.36 | 83.38 |
| 2.11 | Cerium bromide | 4 | 83 | 11.15 | 96.61 | 81.54 |
| 2.12 | Praseodymium bromide | 4 | 83 | 10.38 | 98.22 | 82.62 |
| 2.13 | n(Lanthanum chloride):n(Cerium chloride) = 3:1 | 4 | 83 | 3.17 | 98.68 | 91.38 |

TABLE 1-continued

Experimental results

| Example | Catalyst | Time (h) | Temperature (° C.) | Tar production (%) | Purity (%) | Yield (%) |
|---|---|---|---|---|---|---|
| 2.14 | n(Lanthanum chloride):n(Praseodymium chloride) = 3:1 | 4 | 83 | 4.05 | 98.53 | 89.72 |
| 2.15 | n(Lanthanum chloride):n(Neodymium chloride) = 3:1 | 4 | 83 | 3.64 | 98.60 | 90.14 |
| 2.16 | n(Lanthanum chloride):n(Erbium chloride) = 3:1 | 4 | 83 | 4.51 | 98.56 | 88.31 |
| 2.17 | n(Cerium chloride):n(Praseodymium chloride) = 3:1 | 4 | 83 | 5.13 | 98.63 | 88.26 |
| 2.18 | n(Cerium chloride):n(Neodymium chloride) = 3:1 | 4 | 83 | 4.79 | 98.57 | 89.15 |
| 2.19 | n(Cerium chloride):n(Thulium chloride) = 3:1 | 4 | 83 | 5.27 | 98.52 | 88.27 |
| 2.20 | n(Praseodymium chloride):n(Neodymium chloride) = 3:1 | 4 | 83 | 4.82 | 98.66 | 89.06 |
| 2.21 | n(Praseodymium chloride):n(Erbium chloride) = 3:1 | 4 | 83 | 5.57 | 98.49 | 88.54 |
| 2.22 | n(Praseodymium chloride):n(Holmium chloride) = 3:1 | 4 | 83 | 5.97 | 98.51 | 87.63 |
| 2.23 | n(Cerium chloride):n(Holmium chloride) = 3:1 | 4 | 83 | 4.81 | 98.52 | 89.43 |
| 2.24 | n(Lanthanum chloride):n(Thulium chloride) = 3:1 | 4 | 83 | 5.03 | 98.39 | 87.94 |
| 2.25 | n(Dysprosium chloride):n(Neodymium chloride) = 3:1 | 4 | 83 | 9.22 | 98.17 | 85.96 |
| 2.26 | n(Erbium chloride):n(Thulium chloride) = 3:1 | 4 | 83 | 9.69 | 98.47 | 86.59 |
| 2.27 | n(Lanthanum chloride):n(Cerium chloride):n(Praseodymium chloride) = 3:1:1 | 4 | 83 | 3.93 | 98.71 | 90.26 |
| 2.28 | n(Lanthanum chloride):n(Cerium chloride):n(Neodymium chloride) = 3:1:1 | 4 | 83 | 3.51 | 98.67 | 91.67 |
| 2.29 | Zinc chloride | 4 | 83 | 18.10 | 97.69 | 81.57 |
| 2.30 | Calcium chloride | 4 | 83 | 16.69 | 95.22 | 78.98 |
| 2.31 | Aluminum chloride | 4 | 83 | 25.20 | 92.21 | 75.67 |
| 2.32 | n(Zinc chloride):n(Calcium chloride) = 3:1 | 4 | 83 | 18.58 | 97.60 | 80.22 |
| 2.33 | n(Lanthanum chloride):n(Zinc chloride) = 3:1 | 4 | 83 | 15.69 | 93.61 | 81.24 |
| 2.34 | n(Cerium chloride):n(Calcium chloride) = 3:1 | 4 | 83 | 15.52 | 92.11 | 79.81 |

Figure 3:
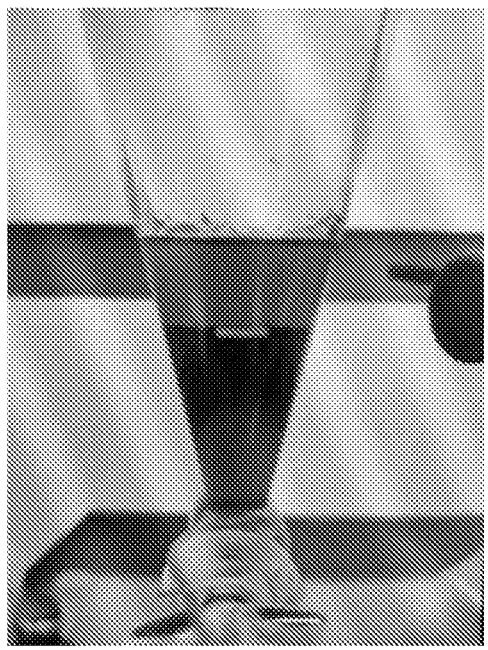
FIG. 3 shows a state of a reaction liquid in a traditional pinacolone preparation process, where an upper transparent layer is a pinacolone solution, and a bottom layer is a mixture of tar and hydrochloric acid; and the tar content is 19% or higher.
Figure 4:
FIG. 4 shows a state of a reaction liquid in a preparation process according to an embodiment of present disclosure involving a catalyst; where the tar content is 5% or less (both an upper layer and a bottom layer are very clear, and the tar impurities are almost absent; and a shadow part is caused by reflection of a glass bottle).

Referring to Table 1, when the catalyst was absent, the tar production was as high as 19.75%. The reaction solution was partially taken out and subjected to standing in a separating flask, which was specifically shown in FIG. 3. A large amount of tar was dissolved in the bottom hydrochloric acid layer, causing a difficulty of hydrochloric acid recycle, and a large amount of waste acid and waste water cannot be solved, resulting in high industrial environmental costs.

When a single lanthanide chloride was added as the catalyst, the tar production was greatly reduced, and the yield and purity of the pinacolone product were greatly improved. Considering the tar production and the yield of the pinacolone product, the single lanthanide chloride was preferably lanthanum chloride and cerium chloride.

When the compounded lanthanide Lewis acid was a combination of a first component and a second component, a molar ratio of the first component to the second component was 3:1, and when the compounded lanthanide Lewis acid was a combination of the first component and the second component, where the second component is a combination of two compounds, a molar ratio of the first component to one of the two compounds to the other of the two compounds was 3:1:1, which were better than the prior art. Referring to results of Table 1, when the first component was selected from the group consisting of lanthanum chloride, cerium chloride, praseodymium chloride and neodymium chloride, and the second component was selected from the group consisting of lanthanum chloride, cerium chloride, praseodymium chloride and neodymium chloride, erbium chloride, holmium chloride, dysprosium chloride, thulium chloride, and a combination thereof, but did not contain the compound selected as the first component, its effects were better than that of the single lanthanide chloride, showing that a combination of two or more lanthanide chlorides and its catalysis had a certain synergistic promoting effect. The tar contents in Examples 2.15, 2.20, 2.22, 2.25, 2.29 and 2.30 were all below 5%, and the whole reaction system was very clean, as shown in FIG. 5.

When the catalyst was zinc chloride, calcium chloride, aluminum chloride, a mixture of zinc chloride and calcium chloride, or a mixture of zinc chloride, calcium chloride and the lanthanide chlorides, its effects were not ideal. The tar dissolved in hydrochloric acid, causing obstacles to recycling the hydrochloric acid, which cannot essentially realize the clean and green production of pinacolone.

Figure 5:
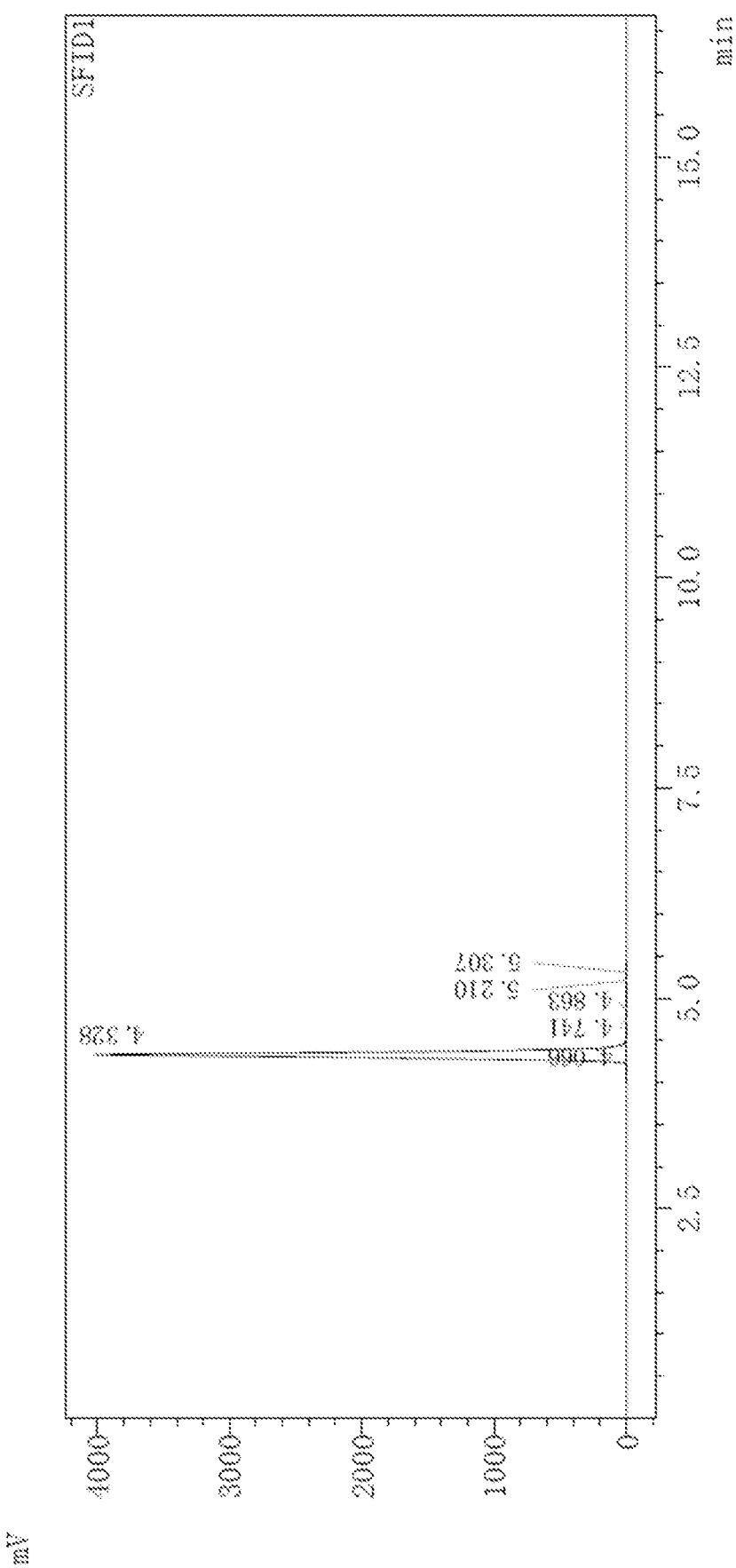
FIG. 5 is a gas chromatogram of a pinacolone product according to Example 2.15 of the present disclosure.

A gas chromatogram of a pinacolone product in Example 2.15 (98.68% purity) was shown in FIG. 5.

Example 3

The preparation process provided herein was basically the same as that in Example 1, where the catalyst was lanthanum chloride; the second reaction was performed at 83° C. for 4 h; and a weight ratio of paraformaldehyde to hydrochloric acid in the paraformaldehyde hydrochloric acid solution was 1:5. Molar ratios of the lanthanum chloride to the 2-methyl-2-butene (e.g., 5:1000, 10:1000, 20:1000, 30:1000, 40:1000 and 50:1000) were employed for the preparation of pinacolone, and the results were shown in Table 2.

TABLE 2

| Example | n(Lanthanum chloride):n(Isopentene) | Time (h) | Temperature (° C.) | Tar production (%) | Purity (%) | Yield (%) |
|---|---|---|---|---|---|---|
| 3.1 | 5:1000 | 4 | 83 | 10.28 | 98.59 | 87.46 |
| 3.2 | 10:1000 | 4 | 83 | 9.91 | 98.54 | 87.21 |
| 3.3 | 20:1000 | 4 | 83 | 8.23 | 98.76 | 89.38 |
| 3.4 | 30:1000 | 4 | 83 | 7.65 | 98.59 | 89.42 |
| 3.5 | 40:1000 | 4 | 83 | 7.93 | 98.61 | 88.65 |
| 3.6 | 50:1000 | 4 | 83 | 8.14 | 98.72 | 89.39 |

Referring to Table 2, the catalyst in this example was the lanthanum chloride. When n(Lanthanum chloride):n(2-methyl-2-butene)=20:1000, this example was performed at 83° C. for 4 h. The tar production was 8.23% (which decreased by 58.31%), the purity of the pinacolone production was above 98.50%, and the yield of the pinacolone was above 88%, showing significant improved effects.

Example 4

The preparation process provided herein was basically the same as that in Example 1, where the catalyst was a mixture of lanthanum chloride and cerium chloride; the second reaction was performed at 83° C. for 4 h; a molar ratio of the lanthanum chloride to the cerium chloride was 3:1; and a weight ratio of paraformaldehyde to hydrochloric acid in the paraformaldehyde hydrochloric acid solution was 1:5. Molar ratios of the mixture of lanthanum chloride and cerium chloride to the 2-methyl-2-butene (e.g., 5:1000, 10:1000, 20:1000, 30:1000, 40:1000 and 50:1000) were employed for the preparation of pinacolone, and the results were shown in Table 3.

TABLE 3

| Example | n(Lanthanum chloride and Cerium chloride):n(Isopentene) | Time (h) | Temperature (° C.) | Tar production (%) | Purity (%) | Yield (%) |
|---|---|---|---|---|---|---|
| 4.1 | 5:1000 | 4 | 83 | 9.28 | 98.52 | 85.16 |
| 4.2 | 10:1000 | 4 | 83 | 7.48 | 98.56 | 83.41 |
| 4.3 | 20:1000 | 4 | 83 | 3.17 | 98.68 | 91.38 |
| 4.4 | 30:1000 | 4 | 83 | 4.25 | 98.60 | 90.67 |
| 4.5 | 40:1000 | 4 | 83 | 3.91 | 98.50 | 88.92 |
| 4.6 | 50:1000 | 4 | 83 | 3.84 | 98.65 | 89.69 |

Referring to Table 3, the catalyst in this example was the mixture of lanthanum chloride and cerium chloride, and n(Lanthanum chloride):n(Cerium chloride)=3:1. When n(The mixture of lanthanum chloride and cerium chloride): n(2-methyl-2-butene)=20:1000, the second reaction was performed at 83° C. for 4 h. The tar production was 3.17% (which decreased by 83.94%), the purity of the pinacolone production was above 98.50%, and the yield of the pinacolone was above 91% (which increased by 17.70%).

Example 5

The preparation process provided herein was basically the same as that in Example 1, where the catalyst is a combination of lanthanum chloride and cerium chloride; a molar ratio of the compounded catalyst to 2-methyl-2-butene was 0.02:1; the second reaction was performed at 83° C. for 4 h; and a weight ratio of paraformaldehyde to hydrochloric acid in the paraformaldehyde hydrochloric acid solution was 1:5. A series of lanthanum chloride-cerium chloride compounded catalysts varying in molar ratio (e.g., 1:10, 1:5, 1:3, 3:1, 5:1, 10:1, 1:20, 1:50, 20:1 and 50:1) were employed for the preparation of pinacolone, and the results were shown in Table 4.

TABLE 4

| Example | n(Lanthanum chloride):n(Cerium chloride) | Time (h) | Temperature (° C.) | Tar production (%) | Purity (%) | Yield (%) |
|---|---|---|---|---|---|---|
| 5.1 | 1:10 | 4 | 83 | 8.34 | 97.86 | 86.94 |
| 5.2 | 1:5 | 4 | 83 | 5.67 | 98.53 | 88.61 |
| 5.3 | 1:3 | 4 | 83 | 5.28 | 98.51 | 87.92 |
| 5.4 | 1:1 | 4 | 83 | 4.93 | 98.59 | 89.47 |
| 5.5 | 3:1 | 4 | 83 | 3.17 | 98.68 | 91.38 |
| 5.6 | 5:1 | 4 | 83 | 5.66 | 98.52 | 88.95 |
| 5.7 | 10:1 | 4 | 83 | 6.34 | 98.57 | 89.24 |
| 5.8 | 1:20 | 6 | 83 | 12.56 | 95.85 | 82.34 |
| 5.9 | 1:50 | 6 | 83 | 15.69 | 95.57 | 81.85 |
| 5.10 | 20:1 | 6 | 83 | 13.53 | 96.41 | 83.05 |
| 5.11 | 50:1 | 6 | 83 | 14.39 | 97.21 | 84.26 |

Referring to Table 4, the catalyst in this example was the combination of the lanthanum chloride and the cerium chloride. When n(Lanthanum chloride):n(Cerium chloride) =1:10-10:1, the tar productions were below 10%, the purities of the pinacolone production were above 98.50%, and the yields of the pinacolone were above 86.94%. When n(Lanthanum chloride):n(Cerium chloride) is outside the range of 1:10-10:1, the tar productions increased significantly, and the purities and the yields of the pinacolone products decreased.

Example 6

The preparation process provided herein was basically the same as that in Example 1, where the catalyst was a combination of lanthanum chloride, cerium chloride and praseodymium chloride; a molar ratio of the compounded catalyst to 2-methyl-2-butene was 0.02:1; the second reaction was performed at 83° C. for 4 h; and a weight ratio of paraformaldehyde to hydrochloric acid in the paraformaldehyde hydrochloric acid solution was 1:5. A series of lanthanum chloride-cerium chloride-praseodymium chloride compounded catalysts varying in molar ratio (3:1:1, 5:1:1, 5:3:3, 5:2:2, 1:1:1, 6:1:1 and 5:4:4) were employed for the preparation of pinacolone, and the results were shown in Table 5.

TABLE 5

| Example | n(Lanthanum chloride):n(Cerium chloride):n(Praseodymium chloride) | Time (h) | Temperature (° C.) | Tar production (%) | Purity (%) | Yield (%) |
|---|---|---|---|---|---|---|
| 6.1 | 3:1:1 | 4 | 83 | 3.93 | 98.71 | 90.26 |
| 6.2 | 5:1:1 | 4 | 83 | 6.67 | 98.53 | 88.61 |
| 6.3 | 5:3:3 | 4 | 83 | 8.16 | 98.51 | 87.92 |
| 6.4 | 5:2:2 | 4 | 83 | 8.93 | 98.59 | 87.47 |
| 6.5 | 1:1:1 | 4 | 83 | 4.66 | 98.62 | 89.55 |
| 6.6 | 6:1:1 | 4 | 83 | 12.66 | 98.20 | 85.95 |
| 6.7 | 5:4:4 | 4 | 83 | 13.22 | 98.24 | 87.80 |

Referring to Table 5, when the catalyst was the combination of lanthanum chloride, cerium chloride and praseodymium chloride, a preferred range was 1-5:1-3:1-3, preferably 1-3:1:1 or 3:1:1.

Example 7

The preparation process provided herein was basically the same as that in Example 1, where the catalyst is a combination of lanthanum chloride and cerium chloride; a molar ratio of the lanthanum chloride to the cerium chloride was 3:1; a molar ratio of the compounded catalyst to 2-methyl-2-butene was 0.02:1; and a weight ratio of paraformaldehyde to hydrochloric acid in the paraformaldehyde hydrochloric acid solution was 1:5. An addition of the paraformaldehyde hydrochloric acid solution lasted for 0.5 h, and the second reaction was performed at 60° C. for 1 h. The tar production, the purity and the yield (based on the 2-methyl-2-butene) of the pinacolone product were analyzed, and an experimental result was shown in Table 6.

Example 8

The preparation process provided herein was basically the same as that in Example 1, where the catalyst was the combination of lanthanum chloride and cerium chloride; a molar ratio of the lanthanum chloride to the cerium chloride was 3:1; a molar ratio of the compounded catalyst to 2-methyl-2-butene was 0.02:1; and a weight ratio of paraformaldehyde to hydrochloric acid in the paraformaldehyde hydrochloric acid solution was 1:10. An addition of the paraformaldehyde hydrochloric acid solution lasted for 1 h, and the second reaction was performed at 70° C. for 3 h. The tar production, the purity and the yield (based on the 2-methyl-2-butene) of the pinacolone product were analyzed, and an experimental result was shown in Table 6.

Example 9

The preparation process provided herein was basically the same as that in Example 1, where the catalyst was the combination of lanthanum chloride and cerium chloride; the molar ratio of the lanthanum chloride to the cerium chloride was 3:1; the molar ratio of the compounded catalyst to 2-methyl-2-butene was 0.02:1; and a weight ratio of paraformaldehyde to hydrochloric acid in the paraformaldehyde hydrochloric acid solution was 1:10. An addition of the paraformaldehyde hydrochloric acid solution lasted for 2 h, and the second reaction was performed at 83° C. for 4 h. The tar production, the purity and the yield (based on the 2-methyl-2-butene) of the pinacolone product were analyzed, and an experimental result was shown in Table 6.

Example 10

The preparation process provided herein was basically the same as that in Example 1, where the catalyst was the combination of lanthanum chloride and cerium chloride; the molar ratio of the lanthanum chloride to the cerium chloride was 3:1; the molar ratio of the compounded catalyst to 2-methyl-2-butene was 0.02:1; and a weight ratio of paraformaldehyde to hydrochloric acid in the paraformaldehyde hydrochloric acid solution was 1:15. An addition of the paraformaldehyde hydrochloric acid solution lasted for 3 h, and the second reaction was performed at 90° C. for 6 h. The tar production, the purity and the yield (based on the 2-methyl-2-butene) of the pinacolone product were analyzed, and an experimental result was shown in Table 6.

Example 11

The preparation process provided herein was basically the same as that in Example 1, where the catalyst was the combination of lanthanum chloride and cerium chloride; the molar ratio of the lanthanum chloride to the cerium chloride was 3:1; the molar ratio of the compounded catalyst to 2-methyl-2-butene was 0.02:1; and a weight ratio of paraformaldehyde to hydrochloric acid in the paraformaldehyde hydrochloric acid solution was 1:20. An addition of the paraformaldehyde hydrochloric acid solution lasted for 2 h, and the second reaction was performed at 80° C. for 5 h. The tar production, the purity and the yield (based on the 2-methyl-2-butene) of the pinacolone product were analyzed, and an experimental result was shown in Table 6.

Example 12

The preparation process provided herein was basically the same as that in Example 1, where the catalyst was the combination of lanthanum chloride and cerium chloride; the molar ratio of the lanthanum chloride to the cerium chloride was 3:1; a molar ratio of the compounded catalyst to 2-methyl-2-butene was 0.02:1; and a weight ratio of paraformaldehyde to hydrochloric acid in the paraformaldehyde hydrochloric acid solution was 1:5. An addition of the paraformaldehyde hydrochloric acid solution lasted for 2 h, and the second reaction was performed at 83° C. for 4 h. The tar production, the purity and the yield (based on the 2-methyl-2-butene) of the pinacolone product were analyzed, and an experimental result was shown in Table 6.

Referring to Table 6, in the second reaction, reaction results were affected by weight ratios of paraformaldehyde to hydrochloric acid, the addition time of the paraformaldehyde hydrochloric acid solution and the reaction time. The weight ratio of paraformaldehyde to hydrochloric acid was preferably 1:5 or 1:10, the addition time of the paraformaldehyde hydrochloric acid solution was not less than 2 h, the reaction time was greater than 4 h, and the reaction temperature was about 83° C.

Example 13

In the industrial production, for the annual 8,000-ton pinacolone output, the preparation method provided herein can reduce the discharge of waste acid by 48,000 tons per year, and save more than 12 million yuan per year. This application facilitated the green and clean production of pinacolone, and greatly promoted the progress of pinacolone industrial production.

Described above are only preferred embodiments of the present disclosure, which are not intended to limit the disclosure. Any modifications and equivalent replacements made within the spirit and principle of the present disclosure shall fall within the scope of this application defined by the appended claims.

What is claimed is:
1. A method for preparing pinacolone, comprising:
reacting raw materials in the presence of a catalyst to produce pinacolone;
wherein the raw materials comprise 2-methyl-2-butene, hydrochloric acid and formaldehyde;
the catalyst is a single lanthanide Lewis acid, a compounded lanthanide Lewis acid, or a lanthanide metal oxide soluble in hydrochloric acid;
the single lanthanide Lewis acid is selected from the group consisting of lanthanum chloride, cerium chloride, praseodymium chloride and neodymium chloride;
the compounded lanthanide Lewis acid is a combination of a first component and a second component; wherein the first component is selected from the group consisting of lanthanum chloride, cerium chloride, praseodymium chloride and neodymium chloride; the second component is selected from the group consisting of lanthanum chloride, cerium chloride, praseodymium chloride, neodymium chloride, erbium chloride, holmium chloride, dysprosium chloride, thulium chloride, and a combination thereof; and the second component is free of a compound selected as the first component;
a molar ratio of the first component to the second component in the compounded lanthanide Lewis acid is 1-50:50-1; and

TABLE 6

| Example | Weight ratio of paraformaldehyde to hydrochloric acid | Addition time (h) | Time (h) | Temperature (° C.) | Tar production (%) | Purity (%) | Yield (%) |
|---|---|---|---|---|---|---|---|
| 7 | 1:5 | 0.5 | 1 | 60 | 9.74 | 97.73 | 85.69 |
| 8 | 1:10 | 1 | 3 | 70 | 8.58 | 98.49 | 86.23 |
| 9 | 1:10 | 2 | 4 | 83 | 4.26 | 98.71 | 92.08 |
| 10 | 1:15 | 3 | 6 | 90 | 5.59 | 96.31 | 88.37 |
| 11 | 1:20 | 2 | 5 | 80 | 8.68 | 98.56 | 87.89 |
| 12 | 1:5 | 2 | 4 | 83 | 3.17 | 98.68 | 91.38 | in a case that the second component is a combination of two compounds respectively selected from the group consisting of lanthanum chloride, cerium chloride, praseodymium chloride, neodymium chloride, erbium chloride, holmium chloride, dysprosium chloride and thulium chloride, a molar ratio of the first component to one of the two compounds to the other of the two compounds is 1-5:1-3:1-3.

2. The method of claim 1, wherein the molar ratio of the first component to the second component in the compounded lanthanide Lewis acid is 1-10:10-1.

3. The method of claim 2, wherein the molar ratio of the first component to the second component in the compounded lanthanide Lewis acid is 1-10:5-1.

4. The method of claim 1, wherein in the case that the second component is a combination of two compounds respectively selected from the group consisting of lanthanum chloride, cerium chloride, praseodymium chloride, neodymium chloride, erbium chloride, holmium chloride, dysprosium chloride and thulium chloride, the molar ratio of the first component to one of the two compounds to the other of the two compounds is 1-3:1:1.

5. The method of claim 4, wherein in the case that the second component is a combination of two compounds respectively selected from the group consisting of lanthanum chloride, cerium chloride, praseodymium chloride, neodymium chloride, erbium chloride, holmium chloride, dysprosium chloride and thulium chloride, the molar ratio of the first component to one of the two compounds to the other of the two compounds is 3:1:1.

6. The method of claim 1, wherein a molar ratio of the catalyst to the 2-methyl-2-butene is 5-50:1000.

7. The method of claim 6, wherein the molar ratio of the catalyst to the 2-methyl-2-butene is 10-50:1000.

8. The method of claim 1, wherein the step of reacting the raw materials in the presence of the catalyst to produce pinacolone comprises:
subjecting the 2-methyl-2-butene and the hydrochloric acid to a first reaction to obtain an intermediate; and
adding the formaldehyde and the catalyst to the intermediate followed by a second reaction to produce pinacolone; wherein the first reaction and the second reaction are performed in a continuous manner.

9. The method of claim 8, wherein the first reaction is performed at 0-10° C. for 60-90 min.

10. The method of claim 8, wherein the second reaction is performed at 60-90° C. for 1-6 h.

11. The method of claim 10, wherein the second reaction is performed at 80-90° C. for 4-6 h.

12. The method of claim 10, wherein an addition of the formaldehyde lasts for 0.5-3 h.

13. The method of claim 12, wherein the addition of the formaldehyde lasts for 2-3 h.

14. The method of claim 8, wherein in the formaldehyde is a formaldehyde aqueous solution or a paraformaldehyde hydrochloric acid solution.

15. The method of claim 14, wherein in the paraformaldehyde hydrochloric acid solution, a weight ratio of paraformaldehyde to hydrochloric acid is 1:5-20.

16. The method of claim 8, further comprising:
cooling a reaction solution obtained from the second reaction to room temperature, followed by standing and layering;
wherein a top layer is a pinacolone product; and a bottom layer is a hydrochloric acid layer, which is adapted to be recycled.

* * * * *